(12) United States Patent
Sims et al.

(10) Patent No.: US 9,827,275 B2
(45) Date of Patent: Nov. 28, 2017

(54) IMMUNOSTIMULATORY COMPOSITIONS AND METHODS OF USE THEREOF

(71) Applicant: Comvita New Zealand Ltd., Paengaroa, Te Puke (NZ)

(72) Inventors: Ian Sims, Lower Hutt (NZ); Jonathan McDonald Counsell Stephens, Tuakau South Auckland (NZ); Ralf Christian Schlothauer, Tauranga (NZ); Swapna Gannabathula, Auckland (NZ)

(73) Assignee: Comvita New Zealand Limited, Te Puke (NZ)

( * ) Notice: Subject to any disclaimer, the term of this patent is extended or adjusted under 35 U.S.C. 154(b) by 0 days.

(21) Appl. No.: 15/217,702

(22) Filed: Jul. 22, 2016

(65) Prior Publication Data

US 2017/0049825 A1    Feb. 23, 2017

Related U.S. Application Data

(63) Continuation of application No. 14/078,278, filed on Nov. 12, 2013, now abandoned, which is a continuation of application No. 13/695,595, filed as application No. PCT/NZ2011/000069 on May 5, 2011, now Pat. No. 8,609,159.

(30) Foreign Application Priority Data

May 5, 2010  (NZ) ........................................ 585118

(51) Int. Cl.
| | | |
|---|---|---|
| *A01N 65/00* | (2009.01) | |
| *A61K 35/644* | (2015.01) | |
| *A61K 9/00* | (2006.01) | |
| *A61K 31/715* | (2006.01) | |
| *A61L 15/28* | (2006.01) | |
| *A61L 15/40* | (2006.01) | |
| *A61K 31/716* | (2006.01) | |
| *G01N 33/566* | (2006.01) | |

(52) U.S. Cl.
CPC .......... *A61K 35/644* (2013.01); *A61K 9/0014* (2013.01); *A61K 31/715* (2013.01); *A61K 31/716* (2013.01); *A61L 15/28* (2013.01); *A61L 15/40* (2013.01); *G01N 33/566* (2013.01)

(58) Field of Classification Search
CPC ...................................................... A61K 36/00
USPC ........................................................ 424/725
See application file for complete search history.

(56) References Cited

U.S. PATENT DOCUMENTS

2011/0082103 A1*  4/2011  Lin ...................... A61K 31/715
                                                           514/54

* cited by examiner

*Primary Examiner* — Michael Meller
(74) *Attorney, Agent, or Firm* — Perkins Coie LLP

(57) ABSTRACT

Immunostimulatory compositions and methods of use are described to either enhance or diminish the immune stimulation effects of a honey or honey isolate by recognition of the presence of type II arabinogalactan compounds and utilising this knowledge to tailor the concentration of such compounds thereby adjusting the immune stimulation effects.

13 Claims, 11 Drawing Sheets

Where n = 6 to 25 and $R^1$ =

Where $R^2$ =

Where $R^3$ =

IMMUNOSTIMULATORY COMPOSITIONS AND METHODS OF USE THEREOF

RELATED APPLICATION(S)

This application claims priority from NZ585118 dated 5 May 2010, the contents of which are incorporated herein by reference.

BACKGROUND ART

Honey used in wound dressings has been extensively discussed and taught in the art.

The applicants co-pending patent application, PCT/NZ2009/000232 teaches about the recent finding that honey in the context of wound dressings heals a wound via three distinct phases being an antimicrobial phase, an immune stimulation phase and an anti-inflammatory phase. As noted in this earlier application, the different phases may occur one after the other or in conjunction with one another, particularly in the case of the antimicrobial and immune stimulation phases. These distinct phases do however appear to be critical in providing the particular wound healing characteristics observed in honey.

This application is primarily centred on the immune stimulation or pro-inflammation phase of healing.

Inflammation is typically considered a negative or to be avoided action in the context of wound healing—i.e. why would you inflame an already inflamed wound? The applicants have found that inflammation at least in the honey wound healing context is in fact beneficial for most wound applications contrary to that expected, particularly when placed in context with the other phases of healing. As well as and distinct to anti-microbial effects, honey appears to prime or kick start the immune system into action via this second phase of healing, a characteristic not uncommon in some contexts with positive outcomes e.g. to address chronic or recalcitrant infections where the natural wound healing process has stalled for some reason or alternatively, to prompt a positive reaction such as that observed when probiotic bacteria are introduced to the gut. Many studies have also been produced showing how humans and animals such as mice primed via an immune stimulatory challenge often survive another microbial challenge better than mice not primed. The actual compound(s) responsible for the inflammatory effects are to the applicant's knowledge not described in the art.

Arabinogalactan (AG) is a biopolymer consisting of arabinose and galactose monosaccharides. Two classes exist in nature being plant arabinogalactans and microbial arabinogalactans.

In plants, AG is a major constituent of many gums including gum arabic, gum gutti and so on. AG is also found in *Echinacea* and other plant matter, typically in the amount of 0.1% weight or 100 µg/ml-200 µg/ml.

AG may be attached to proteins and the resulting arabinogalactan protein (AGP) functions as a signalling molecule between cells.

It should be appreciated from the above that it would be useful to have an identified immune-stimulant compound that may be isolated or selected for when tailoring a composition for medical applications such as topical formulations and which can be manipulated to be used in both the context of treating very sensitive wounds through to chronic or recalcitrant wounds. It is an object of the present to address the foregoing problems or at least to provide the public with a useful choice.

All references, including any patents or patent applications cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents form part of the common general knowledge in the art, in New Zealand or in any other country.

It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Further aspects and advantages will become apparent from the ensuing description that is given by way of example only.

SUMMARY

The application broadly relates to the discovery that honey, particularly honey with non-peroxide antibacterial activity, contains type II arabinogalactan (AG) compounds that act to stimulate or prime the immune system. Based on this knowledge, topical formulations such as wound dressings may be produced to accentuate the pro-inflammatory effect or down regulate the pro-inflammatory effect by altering the amount of AG present. Further, the applicants have also identified a synergy in immune stimulation when honey is fortified with AG.

In some embodiments there is provided a honey isolate containing type II arabinogalactan (AG).

In some embodiments there is provided a honey analogue including a honey isolate containing type II arabinogalactan (AG).

In some embodiments there is provided a honey fortified with a honey isolate containing type II arabinogalactan (AG).

In some embodiments there is provided a composition formulated for topical application to a body area of a patient in need thereof containing:
 (a) a honey isolate containing type II arabinogalactan (AG); or
 (b) a honey analogue including a honey isolate containing type II arabinogalactan (AG); or
 (c) a honey fortified with a honey isolate containing type II arabinogalactan (AG); or
 (d) combinations of the above.

In some embodiments there is provided a method of stimulating the immune system of a patient in need thereof by topical application of a composition to a body area of the patient wherein the composition contains:
 (a) a honey isolate containing type II arabinogalactan (AG); or
 (b) a honey analogue containing a honey isolate containing type II arabinogalactan (AG); or
 (c) a honey fortified with a honey isolate containing type II arabinogalactan (AG); or
 (d) combinations of the above.

In some embodiments there is provided the use of a composition in the manufacture of a composition formulated for topical application for stimulating the immune system of a body area on a patient in need thereof wherein the composition contains:
- (a) a honey isolate containing type II arabinogalactan (AG); or
- (b) a honey analogue including a honey isolate containing type II arabinogalactan (AG); or
- (c) a honey fortified with a honey isolate containing type II arabinogalactan (AG); or
- (d) combinations of the above.

In a seventh embodiment there is provided a method of minimising the immune-stimulatory effects of a honey based topical composition by the step of removing type II arabinogalactan (AG) from the honey in the composition.

In some embodiments there is provided the use of a honey based topical composition with type II arabinogalactan (AG) removed from the honey in the manufacture of a topically administered composition for minimising stimulation of the immune system of a body area on a patient in need thereof.

In some embodiments there is provided a method of treatment of a recalcitrant skin condition on a topical body area on a subject in need thereof by:
- a. application of a composition initially that includes:
  - I. a honey isolate containing type II arabinogalactan (AG); or
  - II. a honey analogue including a honey isolate containing type II arabinogalactan (AG); or
  - III. a honey fortified with a honey isolate containing type II arabinogalactan (AG); or
  - IV. combinations of the above;

and, as skin healing progresses;
- b. applying a honey or honey analogue based composition with type II arabinogalactan (AG) removed from the honey or analogue.

In a tenth embodiment there is provided a method of treatment of a sensitive skin condition on a topical body area on a subject in need thereof by:
- a. applying a honey or honey analogue based composition with type II arabinogalactan (AG) removed from the honey or analogue;

and as skin healing progresses;
- b. application of a composition initially that includes:
  - I. a honey isolate containing type II arabinogalactan (AG); or
  - II. a honey analogue including a honey isolate containing type II arabinogalactan (AG); or
  - III. a honey fortified with a honey isolate containing type II arabinogalactan (AG); or
  - IV. combinations of the above.

In some embodiments, there is provided a method of producing a honey based immune-stimulatory composition by the step of:
- a. testing a series of honey batches for the presence of type II AG compounds;
- b. selecting and blending together honeys based on the test results to form a honey blend with type II AG levels greater than 5 µg/g.

In some embodiments there is provided a method of producing a honey based composition that minimises immune-stimulatory effects by:
- a. testing a series of honey batches for the presence of type II AG compounds;
- b. selecting and blending together honeys based on the test results sufficient to leave less than 5 µg/g type II AG compounds in the honey blend.

In some embodiments there is provided a method of determining the immunostimulatory properties of a honey or honey analogue by measuring the content of type II AG in the honey or honey analogue and wherein:
- a. if the amount of type II AG in the honey or honey analogue is greater than approximately 5 µg/g, a measurable immunostimulatory response is predicted; and,
- b. if the amount of type II AG in the honey or honey analogue is less than approximately 5 µg/g, a measurable immunostimulatory response is not predicted.

In some embodiments there is provided a method of producing an isolate of the type II AG compounds from honey by obtaining a honey and then processing the honey by steps selected from: filtration, ultra-filtration, reverse osmosis, solvent extraction, precipitation, or combinations thereof and collecting a high molecular weight isolate from the processing step.

BRIEF DESCRIPTION OF THE DRAWINGS

Further aspects will become apparent from the following description that is given by way of example only and with reference to the accompanying drawings in which.

DETAILED DESCRIPTION

Figure 1:
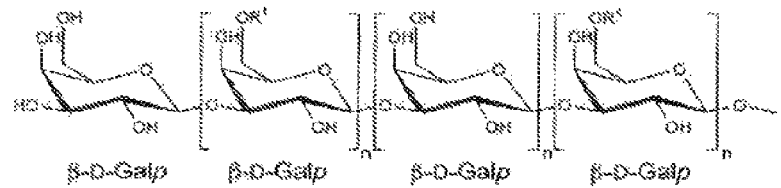
FIG. 1 illustrates a structure of honey-based type II AG compounds.
Figure 1:
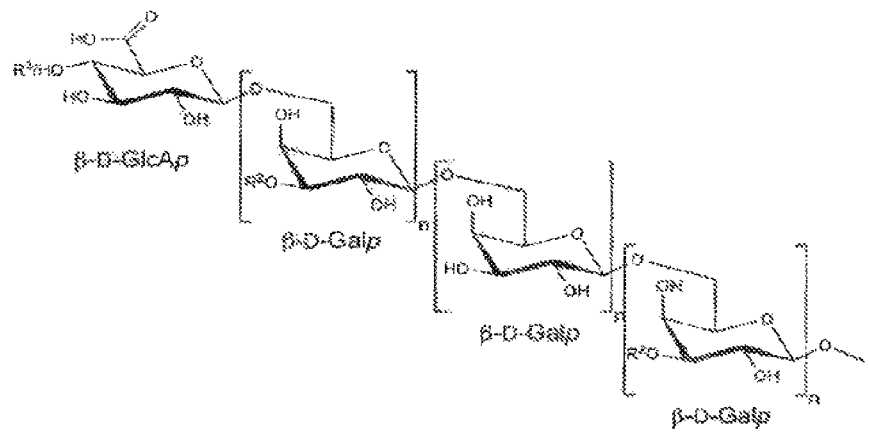
Figure 1:
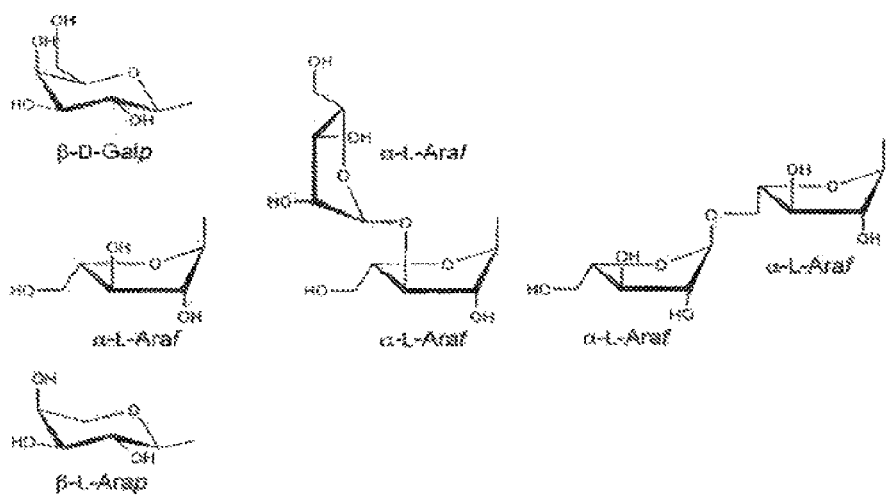
Figure 1:
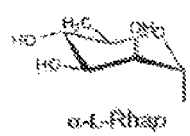

As noted above, the application broadly relates to the discovery that AG compounds are present in honey and, that these compounds are associated with a secondary phase of healing being to stimulate the immune system of the subject to whom the medical formulation is applied. Also, as noted above, the applicants have also identified a synergy in immune stimulation when honey is fortified with AG.

For the purposes of this specification, the term 'arabinogalactan' or 'AG' or grammatical variations thereof refers to biopolymers containing arabinose and galactose monosaccharides.

The term 'type II' when used in reference to AG compounds refers to a family of highly branched polysaccharide compounds rich in galactose and arabinose. They consist of a (1-3)-β-D-galactan backbone having (1-6)-β-D-galactan side chains, which in turn are modified by arabinose. Short arabinose oligosaccharide chains may additionally decorate the galactan backbone.

The term 'arabinogalactan protein' or AGP' or grammatical variations thereof refers to arabinogalactan compounds where the polysaccharide units are attached to multiple sites on a core protein, rich in hydroxyproline.

The terms 'unique manuka factor', 'UMF', 'non-peroxide activity', 'methylglyoxal' or 'MGO' all refer to the antimicrobial activity of a honey above that attributable to the antimicrobial effects of honey pH and osmolarity.

The term 'honey' refers to honey produced either predominantly from one botanical species (monofloral honey) or produced from multiple species and/or mixtures of honey (multifloral honey).

The term 'honey analogue' or grammatical variations thereof refers to a sugar syrup solution that approximates the basic chemical and/or physical properties of natural honey being made up of glucose, fructose, water and hydrogen peroxide and/or glucose peroxidase enzyme.

The term 'isolate' or grammatical variations thereof refers to a composition containing a purified concentration of type II AG compounds separated from a honey as produced in nature or separated from a honey fraction such as a honey UMF fraction or similar.

The term 'secondary phase of healing' refers to an immune stimulant action characterised by the production of inflammatory cytokines including but not limited to TNFα, IL-6 and IL-10.

The term 'wound dressing' refers to a dressing adapted for application to a topical wound containing honey and/or a honey derivative.

The term 'topical' refers to placement on a body area of a subject such as skin as well as mucosal areas such as the oral cavity e.g. gums, the nasal cavity and the vaginal cavity.

The term may also encompass the intestine wall owing to the fact that type II AG compounds are comparatively stable and on oral delivery would reach the intestines chemically intact.

The terms 'chronic' or 'recalcitrant' are used interchangeably to refer to a skin area or broken skin area such as a burn or wound that is either not healing or is only healing slowly despite treatment. This style of healing may be characterised by little macrophage activity at or around the skin area.

The term 'sensitive' or grammatical variations thereof refers to a skin area that the subject finds particularly painful.

The terms 'immunostimulatory', 'stimulate', 'pro-inflammatory' or grammatical variations thereof refer to the subject's immune system being activated to the extent that macrophage cells are present at the wound site and produce cytokines consistent with an inflammatory response including but not limited to TNFα, IL-6 and IL-10.

The terms 'prime the immune system' and/or 'stimulate the immune system' refer to the presence of macrophage cells producing or capable of producing inflammatory related cytokines.

The term 'fortify' or grammatical variations thereof refers to addition of a separate component to a base material and/or the addition of a separate component to increase the concentration of the component already in the base material.

In some embodiments there is provided a honey isolate containing type II arabinogalactan (AG).

The average molecular weight of the AG in the isolate may be from 40,000 to 1,100,000.

The ratio of arabinose to galactose may range from 0.1 to 2.0 parts arabinose to 1.0 parts galactose. The ratio may be 0.65 to 1.21 arabinose to 1.0 parts galactose.

The isolate may include type II AG with a structure as shown in FIG. 1.

The isolate may include greater than 5 µg/g type II AG or sufficient type II AG to cause significant immunostimulatory effects in monocytes. The isolate may include greater than 10 µg/g type II AG.

The honey from which the isolate is derived may be selected from honey's derived form the plant genus *Leptospermum, Kunzea, Weinmannia, Knightia, Metrosideros, Fagus, Trifolium, Myrtaceae*, and combinations thereof. In selected embodiments, the honey may of manuka origin. The honey may be of kanuka origin. The honey may be of clover origin. The honey may instead be a multifloral honey.

In some embodiments there is provided a honey analogue including a honey isolate containing type II arabinogalactan (AG). The analogue may include greater than 10 µg/g type II AG.

In some embodiments there is provided a honey fortified with a honey isolate containing type II arabinogalactan (AG). The honey may be fortified sufficient to increase the concentration of type II AG to greater than 5 µg/g. The concentration may be greater than 10 µg/g.

In some embodiments there is provided a composition formulated for topical application to a body area of a patient in need thereof containing:
  (a) a honey isolate containing type II arabinogalactan (AG); or
  (b) a honey analogue including a honey isolate containing type II arabinogalactan (AG); or
  (c) a honey fortified with a honey isolate containing type II arabinogalactan (AG); or
  (d) combinations of the above.

The composition as described above wherein the patient may be a human. Alternatively, the patient may be a non-human animal.

The composition described above may be formulated as: a dressing, a cream, an ointment, a gel, and combinations thereof.

The type II AG compound(s) described above may be arabinogalactan protein (AGP) compounds.

The composition may include greater than 5 µg/g AG compounds or may include greater than 10 µg/g AG compounds.

In the above embodiments, a non-honey based AG containing composition may be added to the composition. For example a plant based AG compound isolate may be added. Synthetically produced AG compounds may be added. A compound including AG may also be added e.g. grass or an extract thereof.

In some embodiments there is provided a method of stimulating the immune system of a patient in need thereof by topical application of a composition to a body area of the patient wherein the composition contains:
- (a) a honey isolate containing type II arabinogalactan (AG); or
- (b) a honey analogue containing a honey isolate containing type II arabinogalactan (AG); or
- (c) a honey fortified with a honey isolate containing type II arabinogalactan (AG); or
- (d) combinations of the above.

In some embodiments there is provided the use of a composition in the manufacture of a composition formulated for topical application for stimulating the immune system of a body area on a patient in need thereof wherein the composition contains:
- (a) a honey isolate containing type II arabinogalactan (AG); or
- (b) a honey analogue containing a honey isolate containing type II arabinogalactan (AG); or
- (c) a honey fortified with a honey isolate containing type II arabinogalactan (AG); or
- (d) combinations of the above.

In the method or use above, the composition may be formulated for application to a recalcitrant topical body area on a patient.

In some embodiments there is provided a method of minimising the immune-stimulatory effects of a honey based topical composition by the step of removing type II arabinogalactan (AG) from the honey in the composition.

In some embodiments there is provided the use of a honey based topical composition with type II arabinogalactan (AG) removed from the honey in the manufacture of a composition formulated for topical application for minimising stimulation of the immune system of a body area on a patient in need thereof.

In the above method or use, the composition may be formulated for application to a sensitive topical body area on a patient. It should also be noted that the honey based topical composition still provides anti-microbial effects associated with honey even with the isolate removed i.e. anti-microbial effects due to honey are distinct to immune stimulation effects and caused by different components in honey.

In some embodiments of the above method or use, the concentration of type II AG in the honey is less than 5 µg/g or a level that yields no or minimal immunostimulatory effects on monocytes. The level may be less than 1 µg/g type II AG.

As should be appreciated, the above embodiments approach the understanding of the importance of AG in inflammation in two different ways. The immune stimulating embodiments seek to provide a topical formulation that may be applied to skin areas that are not progressing in healing or where only very slow wound healing is occurring. In this context, the AG content in the dressing is maximised. The converse is true in the immune stimulating minimizing embodiments where an inflammatory response may cause considerable pain and discomfort to the subject. In these embodiments the aim is to reduce the content of AG and thereby minimise the inflammatory response while letting other phases of action e.g. anti-microbial and anti-inflammatory provide the primary healing action.

Further, in the above methods and uses, the patient may be a human. Alternatively, the patient may be a non-human animal.

In some embodiments there is provided a method of treatment of a recalcitrant skin condition on a topical body area on a subject in need thereof by:
- a. application of a composition initially that includes:
  - I. a honey isolate containing type II arabinogalactan (AG); or
  - II. a honey analogue including a honey isolate containing type II arabinogalactan (AG); or
  - III. a honey fortified with a honey isolate containing type II arabinogalactan (AG); or
  - IV. combinations of the above;

and, as skin healing progresses;
- b. applying a honey or honey analogue based composition with type II arabinogalactan (AG) removed from the honey or analogue.

In some embodiments there is provided a method of treatment of a sensitive skin condition on a topical body area on a subject in need thereof by:
- a. applying a honey or honey analogue based composition with type II arabinogalactan (AG) removed from the honey or analogue;

and as skin healing progresses;
- b. application of a composition initially that includes:
  - I. a honey isolate containing greater than or equal to 5 µg/g type II arabinogalactan (AG); or
  - II. a honey analogue including a honey isolate containing type II arabinogalactan (AG); or
  - III. a honey fortified with a honey isolate containing type II arabinogalactan (AG); or
  - IV. combinations of the above.

Uses of the above honey or honey analogue based composition with an isolate removed as well as those containing isolates may also be in the manufacture a topical preparation method for the treatment of a recalcitrant or sensitive skin area.

Applying the above to a wound example, the method of treatment may entail initial application of a dressing with pro-inflammatory properties to a new and sensitive wound and then, once the initial healing process begins, removal of the dressing and replacement with a dressing that has inflammatory properties to enhance or speed up the wound healing progression. The opposite may also be the case where the wound is recalcitrant so a pro-inflammatory dressing is applied first and then, once healing progresses, a dressing without pro-inflammatory effects may be applied.

As noted above, the immunostimulatory composition may contain greater than 5 µg/g or greater than 10 µg/g type II AG compounds. Alternatively, if non-immunostimulatory composition may contain less than 5 µg/g or less than 1 µg/g type II AG compounds.

Further, in the above methods and uses, the patient may be a human. Alternatively, the patient may be a non-human animal.

In some embodiments, there is provided a method of producing a honey based immune-stimulatory composition by the step of:
- a. testing a series of honey batches for the presence of type II AG compounds;
- b. selecting and blending together honeys based on the test results to form a honey blend with type II AG levels greater than 5 µg/g.

In the above method, the honey may include kanuka honey.

The honey tested may be produced from a plant or plants selected and/or bred to maximise the level of type II AG compounds in the plant nectar from which the honey is produced. The plant nectar may be selected from the genus: *Leptospermum, Kunzea, Weinmannia, Knightia, Metrosideros, Fagus, Trifolium, Myrtaceae*, and combinations thereof.

Optionally, the composition may include further non-honey based arabinogalactan compounds. For example, a plant based AG compound isolate may be added. Synthetically produced AG compounds may be added. A compound including AG may also be added e.g. grass or an extract thereof.

In some embodiments there is provided a method of producing a honey based composition that minimises immune-stimulatory effects by:
  a. testing a series of honey batches for the presence of type II AG compounds;
  b. selecting and blending together honeys based on the test results sufficient to leave less than 5 µg/g type II AG compounds in the honey blend.

In the above method the honey tested may be produced from a plant or plants selected and/or bred to minimise the level of type II AG compounds in the plant nectar from which the honey is produced. Plant nectar may be selected from the genus: *Leptospermum, Kunzea, Weinmannia, Knightia, Metrosideros, Fagus, Trifolium, Myrtaceae*, and combinations thereof.

In the above methods, the type II AG compound may be AGP.

By way of example, the honeys used in the above embodiments may be selected from honey sources that do not have high levels of AG such as clover honey to make a low AG dressing. Alternatively, high AG containing honeys such as kanuka honeys may be selected to produce a high AG content dressing.

Further, the natural process of producing honey involves bees collecting pollen from flowering plants that is then converted to honey via the bees in the hive. Besides direct manipulation as noted in earlier embodiments of the honey or use of isolates, an alternative may be to alter the plant source of the honey. For example, as noted above *Leptospermum* or *Kunzea* genus trees such as manuka or kanuka trees may be selected and bred to produce higher levels of AG in the plant nectar that the bees then collect and manufacture honey from. Alternatively, plant species (not necessarily from *Leptospermum* or *Kunzea* genus) may be selected for their AG production levels in nectar and the hive placed adjacent these species around flowering in order to concentrate the AG levels in the honey produced by the bees. Examples of alternative species may include *Weinmannia, Knightia, Metrosideros, Fagus, Trifolium* or *Myrtaceae* genus plants.

In some embodiments there is provided a method of determining the immunostimulatory properties of a honey or honey analogue by measuring the content of type II AG in the honey or honey analogue and wherein:
  a. if the amount of type II AG in the honey or honey analogue is greater than approximately 5 µg/g, a measurable immunostimulatory response is predicted; and,
  b. if the amount of type II AG in the honey or honey analogue is less than approximately 5 µg/g, a measurable immunostimulatory response is not predicted.

In the above method, an immune-stimulatory topical formulation may be produced from the honey or honey analogue if the measured type II AG is greater than 5 µg/g. The amount may be greater than 10 µg/g.

In the above method, a non-immune stimulatory topical formulation may be produced from the honey or honey analogue if the measured type II AG is less than 5 µg/g. The amount may be less than 1 µg/g.

In the above method, testing may be completed utilising reactions that involve binding type II AG compounds with specific antibodies. Optionally, one method may be to utilise Enzyme Linked Immuno Sorbent Assay (ELISA) analysis. ELISA may be a useful detection protocol as it is easily implemented in a QA laboratory, can be used to process many samples at once (40-80), provides accurate results and gives a useful degree of detection limit.

In some embodiments there is provided a method of producing an isolate of the type II AG compounds from honey by obtaining a honey and then processing the honey by steps selected from: filtration, ultra-filtration, reverse osmosis, solvent extraction, precipitation, or combinations thereof and collecting a high molecular weight isolate from the processing step.

In some embodiments, the honey or honey analogue may be filtered and the high molecular weight fraction collected so as to increase the concentration of AG in the high molecular weight isolate or to remove the high molecular weight isolate to reduce the AG concentration in the residual honey. In some embodiments, honey may be filtered to obtain a high molecular weight fraction via a 10 kDa filter. In some alternative embodiments, the filter size may be via a 20 kDa filter. In some alternative embodiments, the filter size may be via a 30 kDa filter.

Examples of varying topical ailments to which the formulations described above may be applied include wounds, burns, skin irritations, acne, pustules, skin grafts, ulcers and combinations thereof.

As should be appreciated, the above recognises the importance of a single group of compounds being type II AG compounds in honey and their influence on an immune stimulation phase. The application teaches of an isolate and related AG products that may then be used for a variety of methods and uses. An advantage of product and methods and uses are that natural variations are limited or avoided making the end product more consistent in line with that critical for pharmaceutical/medical applications. In addition, the knowledge around type II AG may be used to tailor medical products for desired applications unlike having to rely totally on nature.

While the above embodiments have been presented separately, it should be appreciated that this is not limiting and aspects of one of the above embodiments may also be applied to other embodiments.

WORKING EXAMPLES

The compositions and methods are now described with reference to examples illustrating embodiments of the composition.

Example 1

In this example, a honey based mixture was formed that had been diluted to negate the sugar effects on microbial survival so that immunostimulatory effects could be observed.

Production of primed macrophage cells i.e. those that produce TNFα were completed by a WST-1 assay to measure the toxic levels of honey samples.

The method was completed as follows.

Artificial honey was prepared by dissolving fructose (192 mg), glucose (80 mg) and sucrose (4 mg) (all three from Sigma Aldrich) in RPMI medium (10 mL) to simulate a 4% (w/v) honey concentration (where the undiluted honey contains 48% fructose, 45% of glucose, 1% of sucrose), filtered by passing through 0.20 µm (DISMIC-13CP) disposable Millipore filter and stored at 4° C. THP-1 cells were harvested, centrifuged and resuspended in RPMI medium giving a concentration of $1 \times 10^6$ cells/mL The cells were then placed in a 96-well plate (Greiner) at 50 µL/well ($5 \times 10^4$ cells/well) and 4, 2, 1, 0.5, 0.25, 0.125, 0.06, 0.03 and 0.15%

(w/v) honey solutions (50.0 µL) were added, resulting in 2, 1, 0.5, 0.25, 0.125, 0.06, 0.03, 0.15 and 0.007% (w/v) final concentrations of honey in 100 µL final volume and incubated for 24 h at 37° C. (Section 2.3.4). The control wells without cells were filled with the RPMI medium. Then 10 µL/well of cell proliferation reagent (WST-1) was added to the cells (i.e. 1:10 dilution) and mixed thoroughly on a shaker for 1 min and the plate was incubated at 37° C. for 1 h. The absorbance of the samples were measured against a background control as blank using a micro plate (ELISA) reader at 450 nm set at a reference wavelength of 620 nm.

The negative control was monocytic leukaemia cells with RPMI medium, and positive control Camptothecin which was used at different concentrations (10 uM, 1 uM, 0.1 uM) to kill the cells.

Figure 2:
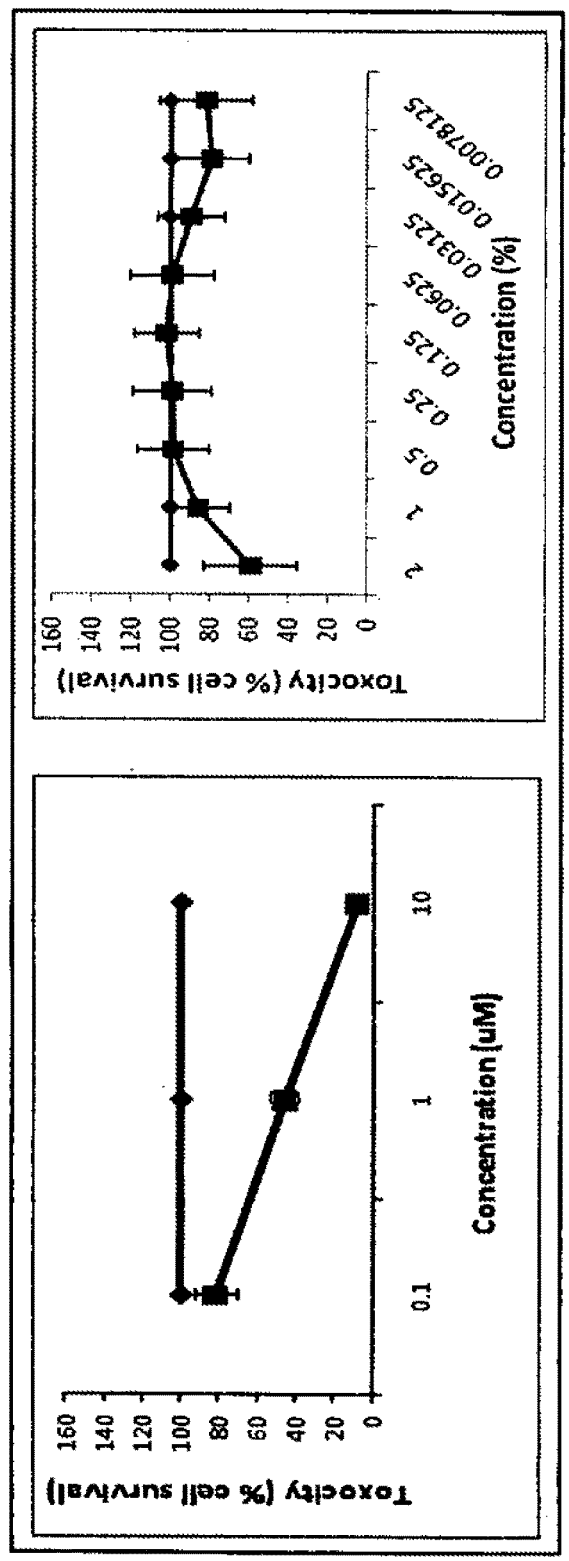
FIG. 2 illustrates the effect of toxicity (cell survival) of THP-1 cells. Cells were treated with in the absence (◇) and presence (□) of Camptothecin (A) and in the absence (◇) and presence (□) of artificial honey solution (B). Data mean of two replicates and the bars displays the standard error (SEM)
Figure 3A:
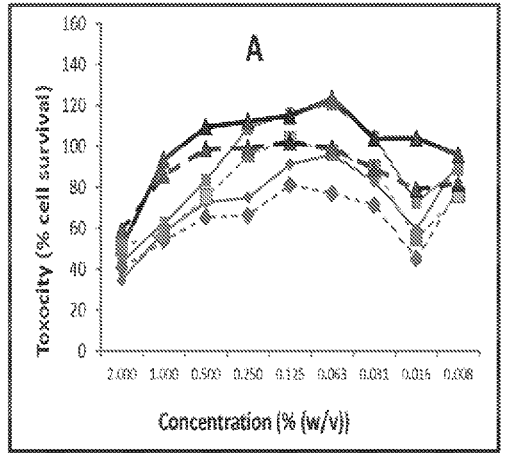
FIGS. 3A-H illustrate the effects of 21 honey samples on cells (A, INTPH 1 and 3; B, 05 and 06; C, 07 and 07; D 10 and 12; E, 14 and 15; F, 16 and 17; G, 18 and 19 and H, 20 and 21 (♦ and ■, respectively)) with measured effects (solid line) compared to standardized effects (relative to sugar control ▲)(dashed line). Data mean of two replicates. Standard errors are not shown.
Figure 3B:
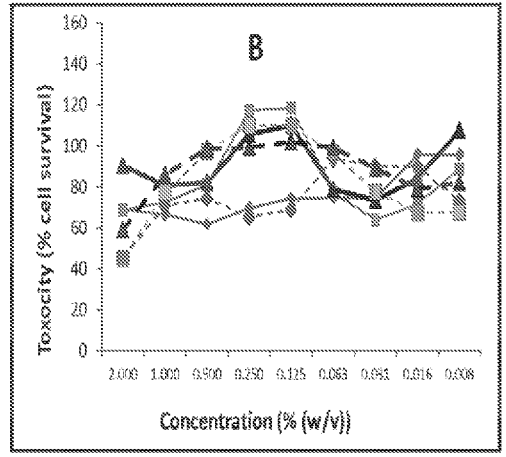
Figure 3C:
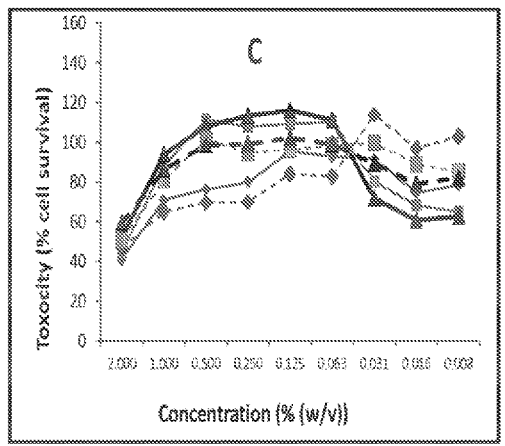
Figure 3D:
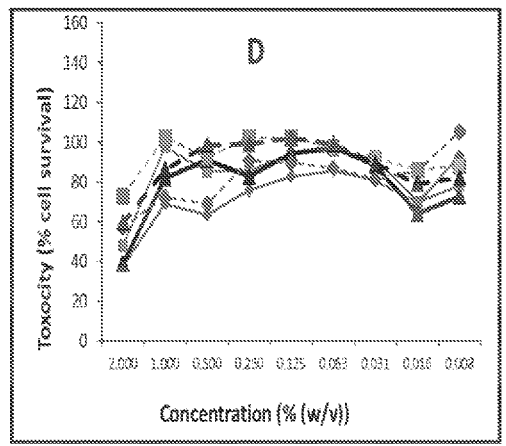
Figure 3E:
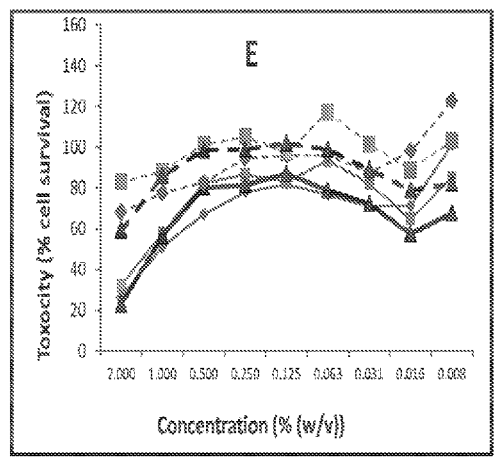
Figure 3F:
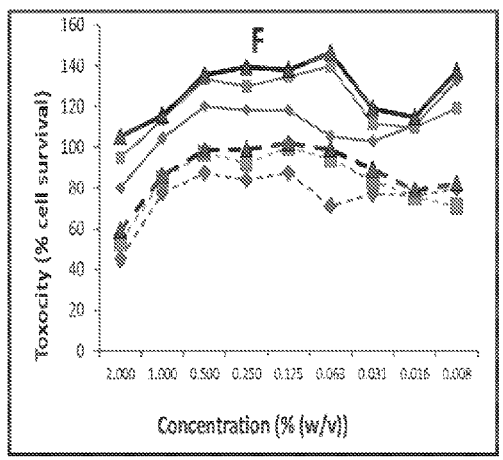
Figure 3G:
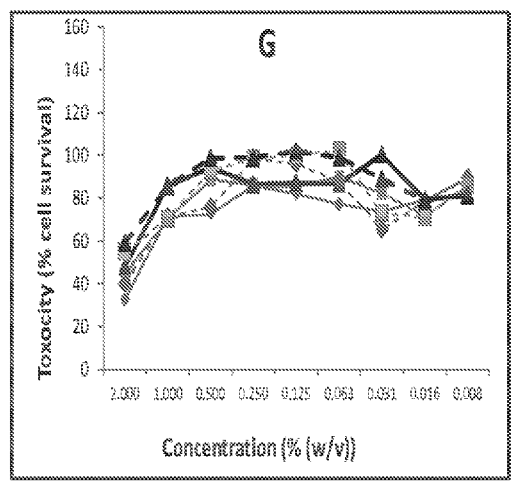
Figure 3H:
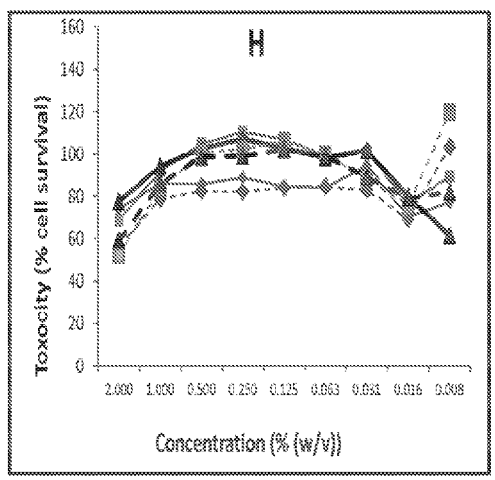

The results show the effect of controls (FIG. 2) and 22 honey samples (FIGS. 3A-H) on cells after 1 hour following the addition of the WST-1 reagent. The artificial honey solution was showing variance on each plate due to the assay. So, the sugar control was standardized against the negative control. Then the effects of the honeys across multiple plates were also standardized against the effects of the artificial honey sugar solution, to remove plate-to-plate variations.

It was observed that the highest honey concentrations tested, 2 and 1% (w/v) honey, reduced cell metabolic activity by as much as 60% of the controls. Thus, it was concluded that both 0.5% and 0.25% concentrations of all honey samples were the highest non-toxic doses that could be used. This was confirmed by re-testing the honeys at 0.5% (w/v), the highest non-toxic concentration.

From the above results it is concluded that some honeys can still show up to 20% toxicity, while some honeys are completely non-toxic effects at 0.5% concentration. In the interests of using the greatest common concentration for multiple honeys for ease of testing, it was decided appropriate to use one concentration for all honey samples. The concentration of 0.5% (w/v) honey is approximately 50 mg/ml was to use for further examples as this allowed cells to grow at a moderate rate without an immediate kill effect.

Macrophage cells were then matured to a point where they were primed and ready to respond to an input. Adding varying levels of LPS and measuring the cytokine TNFα response confirmed the maturity and readiness of the macrophage cells. A standard dose response was found i.e. the larger the LPS dose, the larger the cytokine response.

A variety of different honeys were then added to the primed macrophage cells and the cytokine response measured to determine if there were any trends. ethylglyoxal (MGO) was also added with or without honey to determine if this ingredient of manuka honey also influenced the immune stimulation effects. A sugar solution was also used to determine if this had any effect as well.

Figure 4:
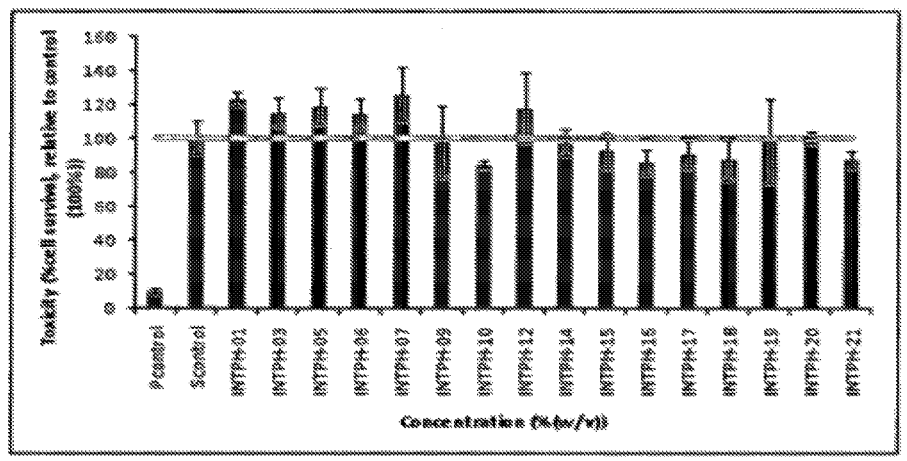
FIG. 4 illustrates the cytoxicity effects of all 18 honey samples (5% (w/v) (■) expressed relative to negative control (100%) (--) and positive control (10 µM camptothecin) (■). Data mean of two replicates and the bars displays the standard error (SEM)
Figure 5A:
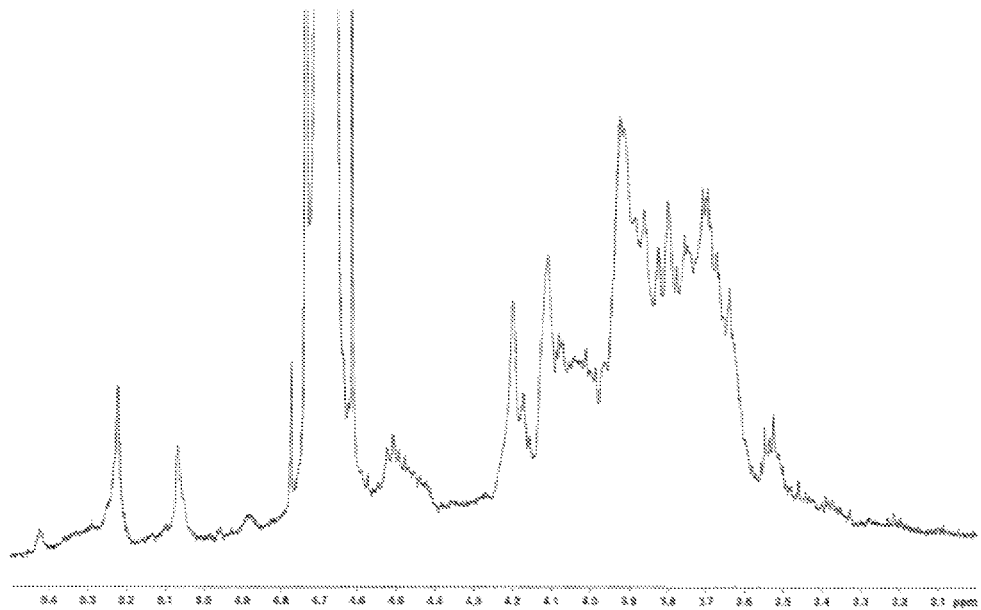
FIGS. 5A-E illustrate five proton NMR spectra of (A) H01, (B) H03, (C) H15, (D) H16 and (E) H20.
Figure 5B:
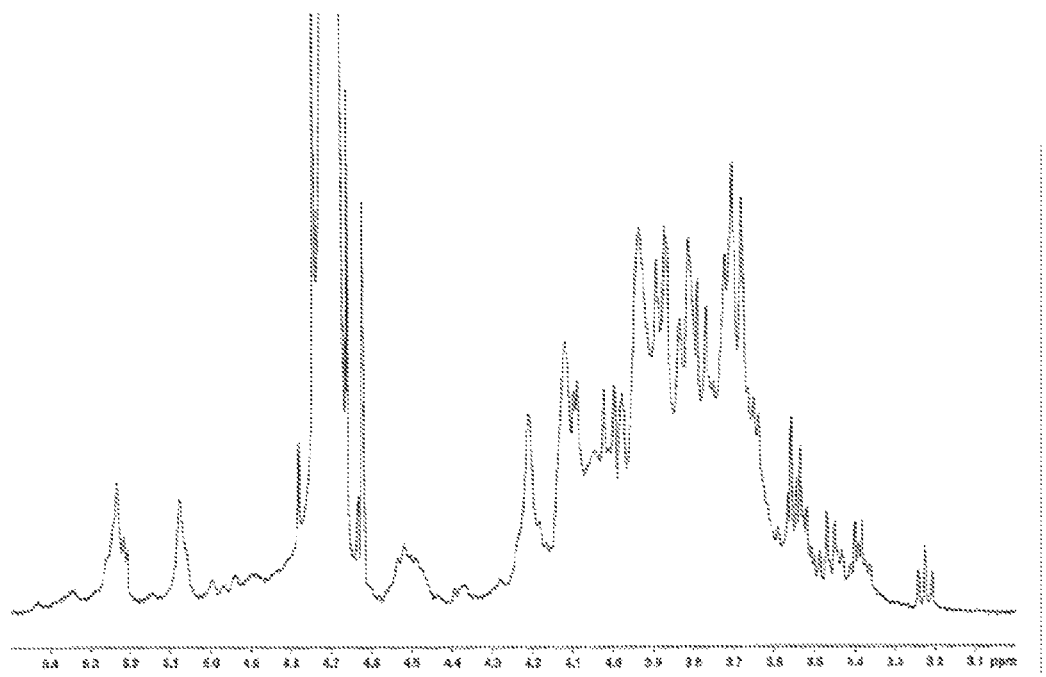
Figure 5C:
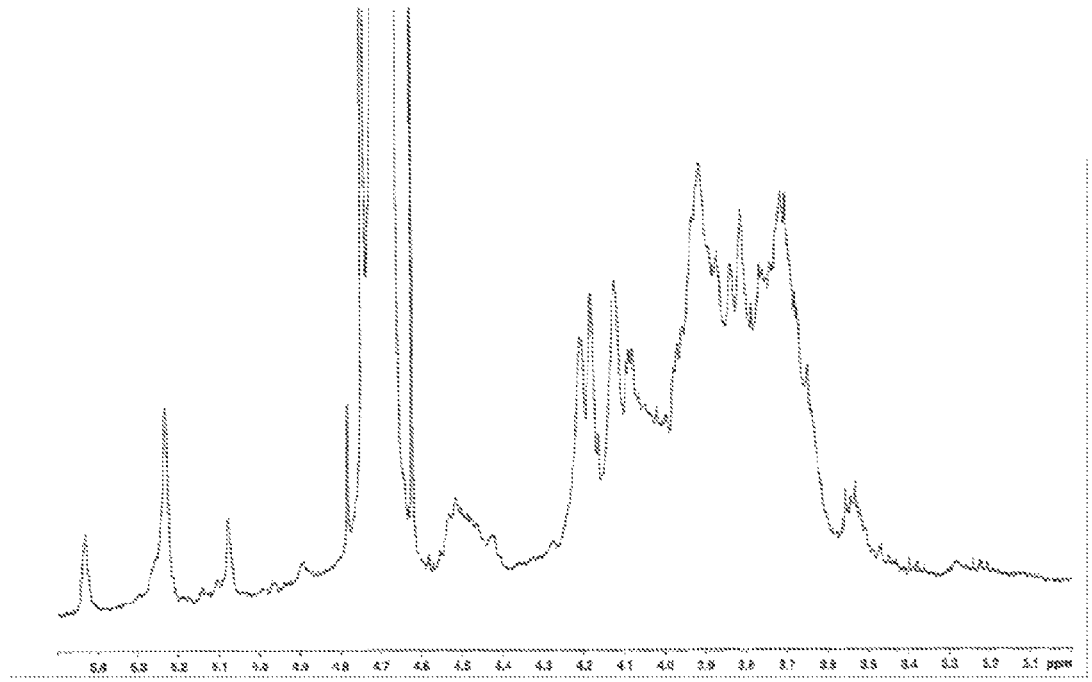
Figure 5D:
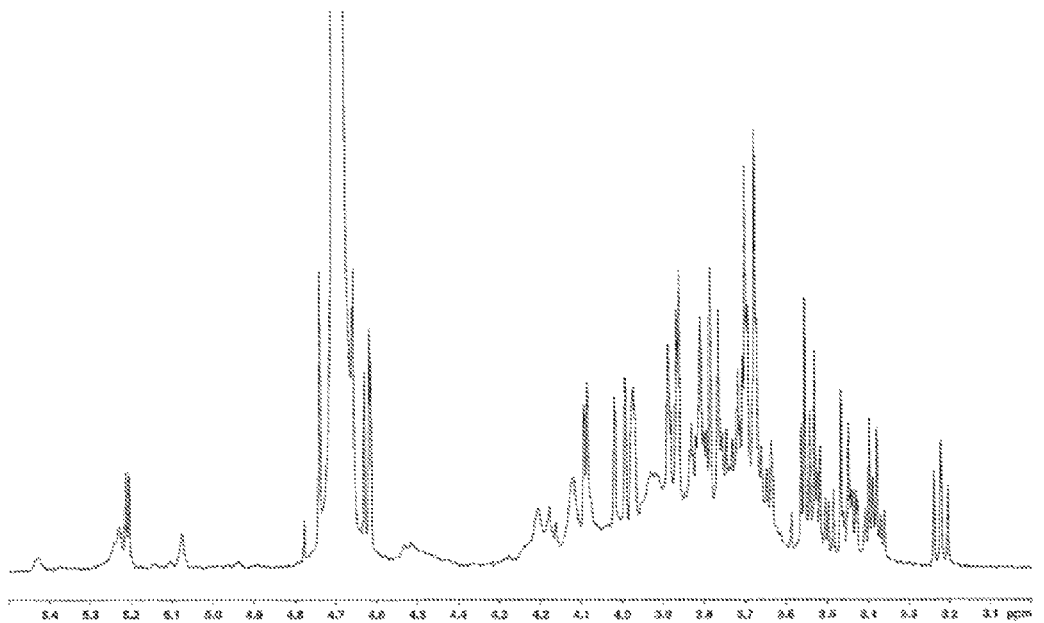
Figure 5E:
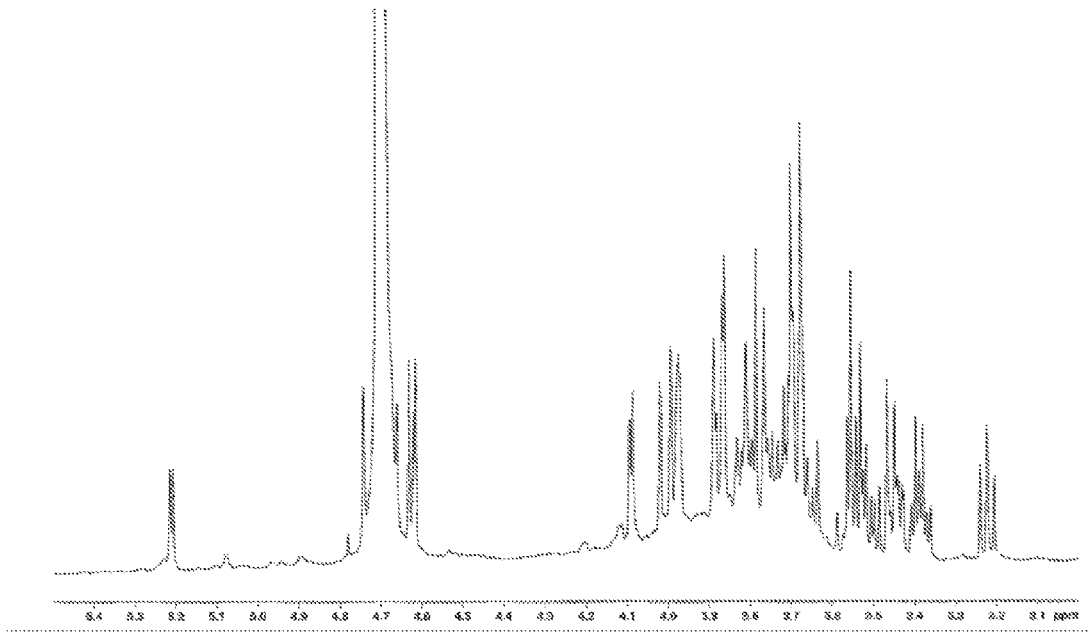

The results found are shown in FIG. 4 where INT-01=0.5 year old northland manuka honey; INT-03=5 year old northland manuka honey; INT-12=0.3 year old east coast manuka honey; INT-15=1.5 year old northland kanuka honey; INT-16=2.5 year old Waikato manuka honey; INT-19=1.5 year old unknown source manuka honey; INT-20=1 year old south island clover honey.

As illustrated, both MGO and sugar alone had no impact on immune stimulation and instead another component of honey present in the manuka and kanuka samples tested was responsible for the pro-inflammatory response.

Some art suggests the presence of LPS in honey may contribute to the observed immune stimulation response. The honey's tested by the applicants were analysed for LPS content however once dilutions were taken into consideration, the confounding effect of LPS is minimal with a maximum of 1 ng LPS being detected in the samples, being vastly less than that required to establish the response observed in the LPS dose response tests completed above.

In conclusion, the pro-inflammatory effects observed, particularly from kanuka and manuka honeys must be due to a compound(s) within these honey and is not attributable to art compounds such as sugar content, MGO content or LPS content in the honey.

Example 2

Heating honey is a practice employed by some beekeepers. Heating manuka honey in particular has been found to increase the MGO content (and price) of the honey although to the detriment of other compounds in the honey. Heat is also associated with the production of contaminating compounds in honey as well. Heat is also well known to break down certain compounds and reduce activity.

The effect of heat on the pro-inflammatory response noted in Example was tested.

Honey samples (5% (w/v) and LPS (1000 ng/mL) were prepared in water and heated at 80° C. for 30 min in a shaking water bath. After heat processing, further dilutions were performed in RPMI medium and the resulting honey tested for cytokine response.

The results were highly compelling in that the rate of cytokine production decreased by approximately 40% in samples that had been heated. This result shows that the compound(s) responsible for the observed pro-inflammatory response are somewhat heat sensitive but have some resistance to heat as well. In view of this observation, compound(s) were identified as not being more sensitive protein or enzymatic actives but instead more likely to be one or more larger chemical compounds that are at least in part chemically modified by heat.

Example 3

In this example, honey found to have pro-inflammatory activity in Example 1 were filtered to 10 kDa and the resulting filtrate (less than 10 kDa) tested to determine if the compound(s) responsible for the pro-inflammatory effects were still present or not. The filtrate tested negative for pro-inflammatory response hence the active compound(s) must have been larger sized (greater than 10 kDa) being of a high molecular weight size.

Example 4

In this example, the pro-inflammatory response honey samples were irradiated to determine if the effects were influenced by irradiation. Irradiation is known in the art to reduce activity of honey, particularly where the activity is due to larger chemical compounds and/or biologically active compounds in the honey. The trial identified an approximately 30% reduction in pro-inflammatory effect between samples without irradiation and those with irradiation. This result is in line with that observed for heat in Example 2 where the pro-inflammatory response reduces although not totally supporting the fact that the compound(s) responsible have some stability and are not sensitive compounds such as active enzymes.

Example 5

In this example, the amount and nature of the high molecular weight compound(s) were determined.

Method

Five honey's were tested being labelled H01=0.5 year old Northland manuka honey; H03=5 year old Northland manuka honey; H15=1.5 year old Northland kanuka honey; H16=2.5 year old Waikato manuka honey and H20=1 year old South Island clover honey.

Each honey was separated using centrifugal ultrafilters (10 kDa molecular weight cut-off) and the retentate collected being the 10 kDa or greater fraction (termed hereafter as the high molecular weight (HMW) fraction.

Retained monosaccharides, present in the HMW fractions, were analysed by high-performance anion-exchange chromatography (HPAEC).

Neutral constituent sugar compositions of the HMW fractions were determined by gas chromatography-mass spectrometry (GC-MS) of alditol acetate derivatives after hydrolysis of the polysaccharides present to their component monosaccharides. Identifications were based on peak retention times and by comparison of electron impact mass spectra with standard spectra.

Glycosyl linkage compositions were determined by GC-MS of partially methylated alditol acetate derivatives. Each sample was analysed in duplicate.

High molecular weight honey fractions (0.25 mg) were methylated using NaOH and $CH_3I$ in DMSO. The methylated polysaccharides were hydrolysed with 2.5 M TFA (200 μL, 1 h, 121° C.), concentrated to dryness under an air stream at 40° C., then reduced with 1.0 M $NaBD_4$ in 2.0 M $NH_4OH$ (200 μL) overnight at 25° C. The reaction was stopped by the addition of glacial acetic acid (50 μL). Borate was removed as volatile trimethylborate by addition of 5% v/v acetic acid in MeOH (3×0.5 mL), and concentrating under an air stream at 40° C., followed by addition of MeOH (3×0.5 ml) and concentrating to dryness under an air stream at 40° C. The resulting alditols were acetylated in acetic anhydride (100 μL) and TFA (100 μL) for 30 min at 50° C. and extracted into $CH_2Cl_2$ for analysis. The partially methylated alditol acetate derivatives were separated by GC on an Agilent HP-5MS fused silica capillary column and analysed by MS using a Hewlett Packard 5973 MSD. Identifications were based on peak retention times and by comparison of electron impact mass spectra with standard spectra. Linkage compositions are expressed as mole percent of the total linkages detected.

The HMW fractions were dissolved in $D_2O$ (deuterium oxide) (0.6 mL) and transferred to 5 mm NMR tubes. NMR spectra were recorded on a Bruker 500 MHz spectrometer at 30° C.

The size-exclusion (SEC) system consisted of a Waters 2690 Alliance separations module, a Waters 450 variable wavelength detector set at 280 nm and a Waters 2410 refractive index monitor. Samples (1 mg mL-1) were centrifuged (13,500 rpm, 5 min) before injection (100 μL) and eluted with 0.1 M $LiNO_3$ containing 0.02% $NaN_3$ (0.7 mL min-1) from two columns (TSK-Gel G5000PWXL and G4000PWXL, 300×7.8 mm, Tosoh Corp., Tokyo, Japan) connected in series. Molecular weights were estimated by comparison of the peak elution volumes with those of pullulan standards.

Results

Fractionation of the honey samples resulted in yields of the >10K MW material of between 1.5 and 4.5 mg, representing 0.03% and 0.06% of the original honey.

Honey samples H16 and H20 included considerable amounts of glucose and fructose as retained by the ultrafiltration membranes. This is reflected in both the higher amount of glucose detected in the constituent sugar analysis and sharp signals in the NMR spectra of these samples. The other samples contained much lower amounts of free monosaccharides.

Neutral constituent sugar analysis showed that the HMW fractions of the honey samples contained between 14 and 27% w/w carbohydrate (Table 1). The analyses showed the presence of arabinose and galactose in the fractionated honey samples. These sugars were present in higher amounts in the manuka and kanuka honeys, than in the clover honey. The presence of glucose probably reflects the presence of free glucose, as determined by HPAEC.

Detection of mannose (as mannitol hexaacetate) in the samples may be from glycoproteins present in the high molecular weight fractions of the honeys, or could result from the reduction of free fructose in the samples to mannitol and glucitol during the preparation of the alditol acetates.

(Note: sample H01 was analysed separately from the other samples and the higher arabinose and galactose contents observed may be due to differences obtained in standard sugar response factors in this analysis.)

TABLE 1

Constituent sugar composition of the high molecular weight fractions of honey samples analysed using the reductive hydrolysis method.

| Sample | Constituent sugars (dry weight %)* | | | | |
| --- | --- | --- | --- | --- | --- |
| | Ara | Man | Glc | Gal | Total |
| H01 | 7.4 | 2.8 | 1.4 | 10.8 | 22.4 |
| H03 | 4.1 | 1.5 | 2.0 | 6.4 | 14.0 |
| H15 | 4.5 | 1.5 | 0.5 | 8.4 | 14.9 |
| H16 | 4.9 | 2.4 | 10.7 | 9.1 | 27.1 |
| H20 | 0.9 | 3.2 | 10.3 | 2.6 | 17.0 |

*Values are the averages of duplicate analyses

Glycosyl linkage analysis revealed the presence of arabinose and galactose in the fractions indicating the presence of arabinogalactan (AG).

Type 1 AGs are usually found as neutral side-chains on plant cell-wall pectic polysaccharides, while Type II AGs are often present as AG-proteins (AGPs), rich in hydroxyproline.

In order to determine whether Type 1 or Type II AGs were present in the honeys, the glycosyl linkage compositions of the samples were determined (Table 2).

The glycosyl linkage analyses of the manuka and kanuka honeys (H01, H03, H15 and H16) were consistent with polymers comprised of a highly branched backbone of 1,3-linked Galp residues, with side-chains made up of Araf-containing oligosaccharides, typical of Type II AGs. These linkages represented 7-10% of the total weight of the HMW fractions from the manuka and kanuka honeys, which was consistent with, but slightly lower than, that calculated from the sum of arabinose and galactose in the constituent sugars analyses (Table 1).

The glycosyl linkage analysis of the clover honey also showed the presence of Type II AGs, but in much lower amounts (1.3% of the weight of the HMW fraction, compared with 3.5% from the sum of arabinose and galactose).

TABLE 2

Glycosyl linkage composition of the high molecular weight fractions of honey samples analysed by GC-MS of partially methylated alditol acetates.

| Sugar | linkage | Linkage composition (mol %)[a] | | | | |
|---|---|---|---|---|---|---|
| | | H01 (9.8%[b]) | H03 (10.0%[b]) | H15 (12.0%[b]) | H16 (12.0%[b]) | H20 (4.0%[b]) |
| Arap | terminal | — | 1.7 | 0.1 | 0.3 | — |
| Araf | terminal | 27.5 | 24.6 | 30.8 | 31.1 | 12.9 |
| | 2- | 3.4 | 4.2 | 2.1 | 2.3 | — |
| | 3- | 1.2 | 1.9 | 1.7 | 2.3 | — |
| | 5- | 4.5 | 6.6 | 5.4 | 8.5 | 6.7 |
| Galp | terminal | 4.2 | 1.4 | 6.8 | 3.3 | 2.1 |
| | 3- | 8.0 | 4.8 | 9.9 | 7.1 | 4.7 |
| | 6- | 5.1 | 5.9 | 4.1 | 2.4 | 2.1 |
| | 3,6- | 27.5 | 27.1 | 23.8 | 22.5 | 7.6 |
| | 3,4,6- | 1.3 | — | 5.4 | 3.1 | — |
| Glcp | terminal | 7.5 | 6.7 | 4.7 | 7.2 | 35.9 |
| Manp | 2- | 4.8 | 3.3 | 3.2 | 3.7 | 15.3 |
| | 3,6- | 1.4 | 1.0 | 0.9 | 0.7 | 5.4 |
| Other | | 3.6 | 10.8 | 1.1 | 5.8 | 7.3 |
| Total | | 100 | 100 | 100 | 100 | 100 |

[a]Values are the averages of duplicate analyses
[b]Values in parentheses are % carbohydrate content calculated from sum of all linkages, compared to internal standard of myo-inositol (10 g)

The 1H NMR spectra of HMW honey fractions revealed in the protein NMR spectroscopy are shown in FIGS. 5A to 5E. The spectra for H16 (FIG. 5D) and H20 (FIG. 5E), that contained high amounts of free sugars showed sharp signals at about 5.21 and 4.61 ppm, that were attributed to H-1 of - and -Glc, respectively. Samples H01 (FIG. 5A), H03 (FIG. 5B), H15 (FIG. 5C) and H16 showed H-1 signals at 5.23 and 5.08 ppm, with H15 and H16 showing an addition H-1 signal at 5.43 ppm. These H-1 signals were consistent with NMR assignments of -L-Araf residues of AGs. Several other H-1 signals were observed in 4.4-4.6 ppm range that were assigned to H-1 of -D-Galp residues. These data provide further evidence for the presence of Type II AGs, probably present as AGPs.

Figure 6:
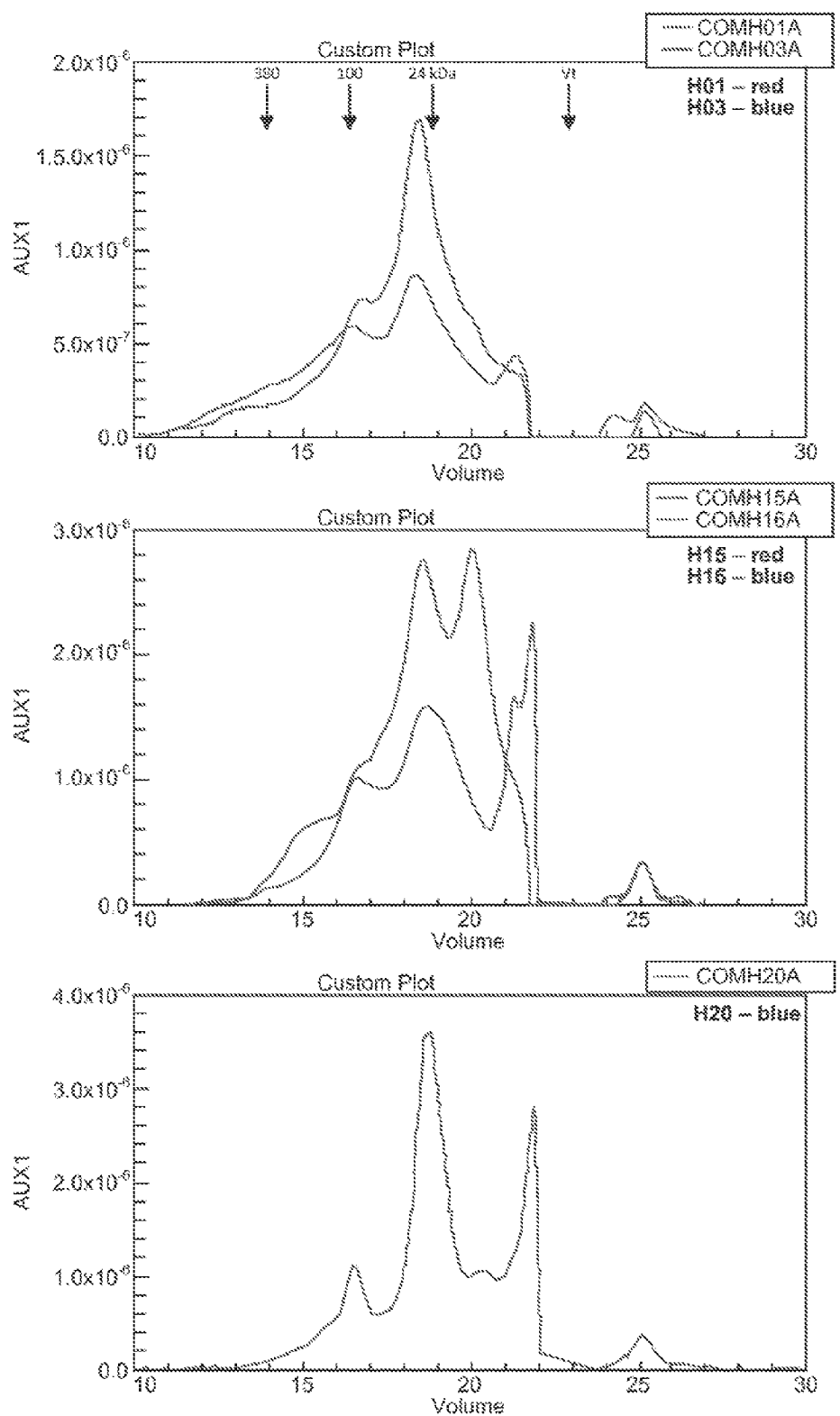
FIG. 6 illustrates size exclusion chromatography (SEC) profiles of high molecular weight honey fractions.

The HMW fractions of the honeys showed complex chromatograms on size exclusion chromatography (SEC) eluting from the $V_0$ to the $V_t$ of the columns (FIG. 6). Sample H01 showed a predominate peak (~18.5 mL) eluting just before the 24 kDa pullulan standard and a second smaller peak (~16.7 mL) eluting just after the 100 kDa pullulan. Similar peaks were also observed for H03, but in smaller amounts. H15, H16 and H20 also showed peaks eluting at ~18.5 and ~16.7 mL (24 kDa and 100 kDa, respectively), but H15 also showed a peak at 20 mL, eluting after the 24 kDa standard. Additionally H16 and H20 showed peaks at 21-22 mL, assumed to be due to low molecular weight sugars present in these samples (see Table 2).

Conclusions

Size fractionation of five honey samples analysed with 10 kDa centrifugal fitters gave high molecular weight (HMW) fractions that represented 0.03-0.09% by weight of the total honeys. The carbohydrate content of these HMW fractions was between 14 and 27% w/w and constituent sugar analysis showed that in four samples (manuka: H01, H03; kanuka: H15, H16) arabinose and galactose accounted for the majority of this carbohydrate. In sample H20 (clover), these sugars accounted for only about 20% of total carbohydrate.

Glycosyl linkage and NMR spectroscopic analysis showed that the honeys contained type II arabinogalactans (AGs), that are often present as arabinogalactan proteins (AGPs). The basic structure is shown in FIG. 1.

Based on the yields of the HMW fractions and their sugar compositions, it is estimated that the type II AG content of the honey samples is approximately:
H01: 0.007%
H03: 0.009%
H15: 0.008%
H16: 0.004%
H20: 0.002%

Example 6

Figure 7:
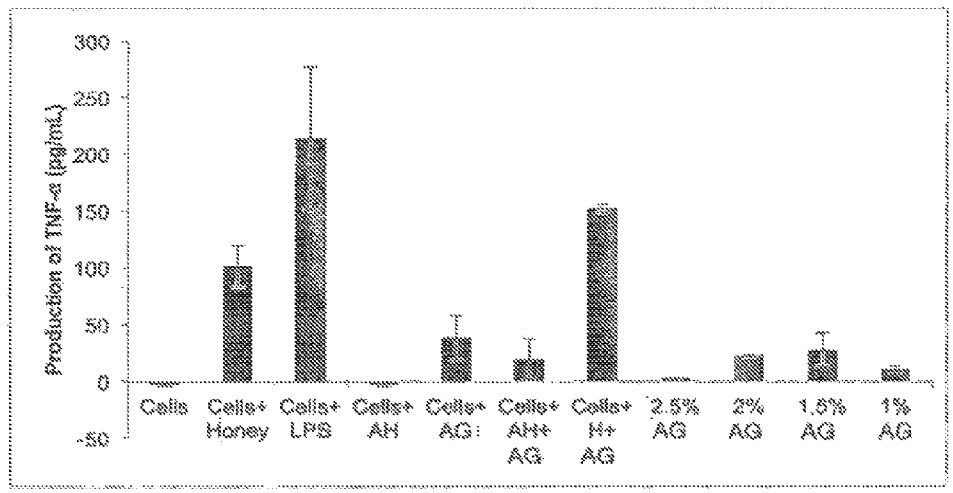
FIG. 7 illustrates results for a trial testing the pro-inflammatory response attributable to arabinogalactans where H=honey; AH=artificial honey; AG=arabinogalactans (type 1); AG=Arabinogalactan concentrations from 2.5% to 1% which is equivalent to honey concentration (i.e. 10% of honey contains 8 µg of AG, 2.5% contains 2 µg, 2%=1.6 µg, 1.5%=1.5 µg and 1%=1 µg of AG)

The above finding the arabinogalactans are the compounds present in the high molecular weight fraction suggests that these compounds are responsible for the pro-inflammatory response observed in earlier examples. This trial tested this hypothesis by testing the pro-inflammatory response of the controls being cells and honey and cells and LPS against varying levels and concentrations of arabinogalactans both with and without honey. The results are shown in FIG. 7.

The results show that arabinogalactans clearly are responsible for the pro-inflammatory effect observed in certain honey. Samples that had arabinogalactans had a far greater proinflammatory response than samples without. The arabinogalactans could be used either on its own (not type II) and still gave a positive pro-inflammatory effect or could be 'spiked' into honey to give a great pro-inflammatory effect. This result shows that it is possible to produce honey based dressings that include tailored levels of arabinogalactans which may be used to tailor the pro-inflammatory effects of the dressing for example by adding more arabinogalactans to increase the effect and conversely, remove arabinogalactans to reduce the pro-inflammatory effect.

Example 7

In this example the ability of three New Zealand honeys to elicit the release of TNF-α from the monocytic cell lines THP-1 and U937 were investigated and the bioactive component responsible identified.

Figure 8:
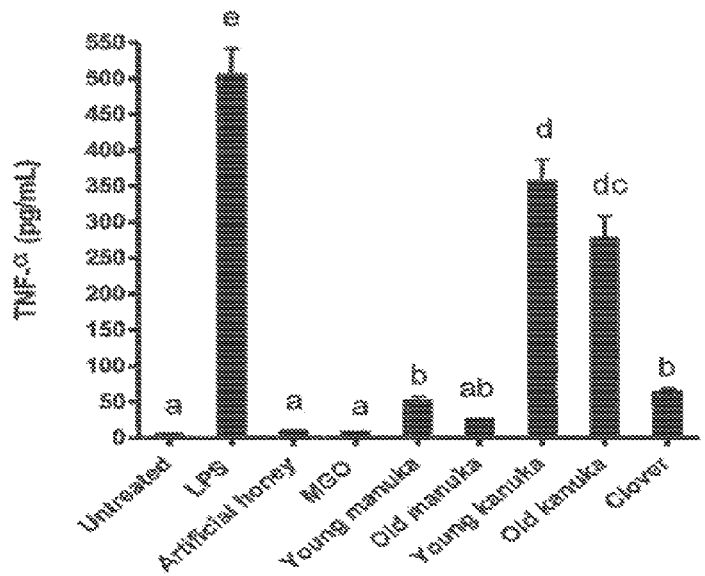
FIG. 8 illustrates a. graph showing cytokine production of THP-1 cell line when contacted with various honeys, a honey analogue and MGO.

The study identified that kanuka, manuka, and clover honeys each stimulated TNF-α release from PMA-differentiated THP-1 cells. Kanuka honey gave the most potent inflammatory effects as illustrated in FIG. 8 although all honeys tested (manuka and clover as well) exhibited some degree of inflammatory effects. A honey analogue was also tested that gave no significant proinflammatory response. Further, a pure MGO sample was also tested which also gave no significant pro-inflammatory response. The results particularly for MGO demonstrate that the proinflammatory effect is not correlated to MGO content in honey or the anti-microbial activity of a honey as measured by UMF activity or non-peroxide activity.

Figure 9:
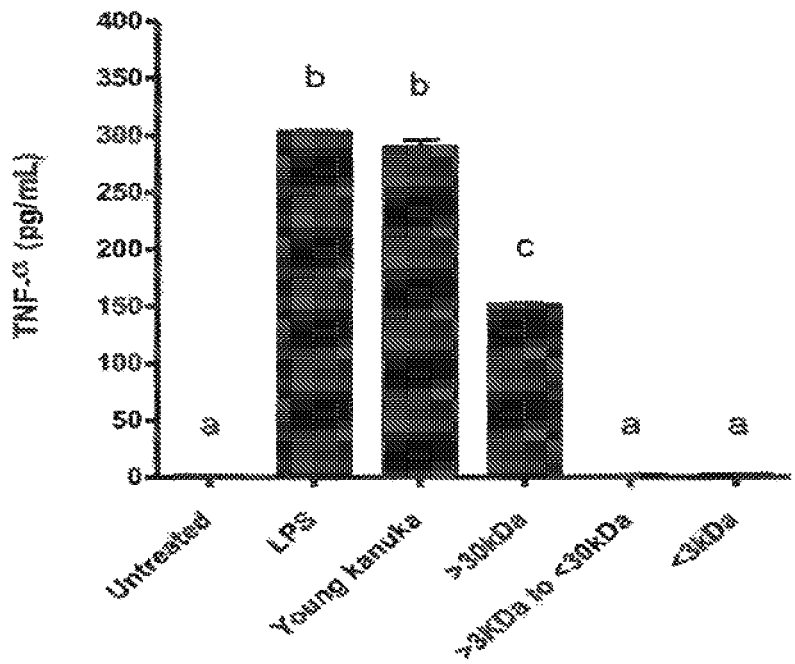
FIG. 9 illustrates a graph showing cytokine production of THP-1 cell line when contacted with varying size kanuka fractions.

The major immunostimulatory activity of kanuka honey was associated with a high molecular weight (>30 kDa) component that was inhibited by polymyxinB B and partially heat-labile. FIG. 9 illustrates the results found for fractions of kanuka honey showing how the active compound is of a comparatively high molecular weight.

LPS levels in the honeys did not adequately explain the level of immunostimulatory activity suggesting that an additional factor was present. The contribution of a type II arabinogalactan protein (AGP) previously identified in kanuka honey was tested. The kanuka AGP stimulated the release of TNF-α from THP-1 and U937 cells, and appears to be largely responsible for the activity of kanuka honey.

Example 8

In this example, the effect or otherwise of pure AGP was analysed to determine how AGP influences cytokine stimulation as exemplified by TNF-α production from THP-1 cell line.

Figure 10:
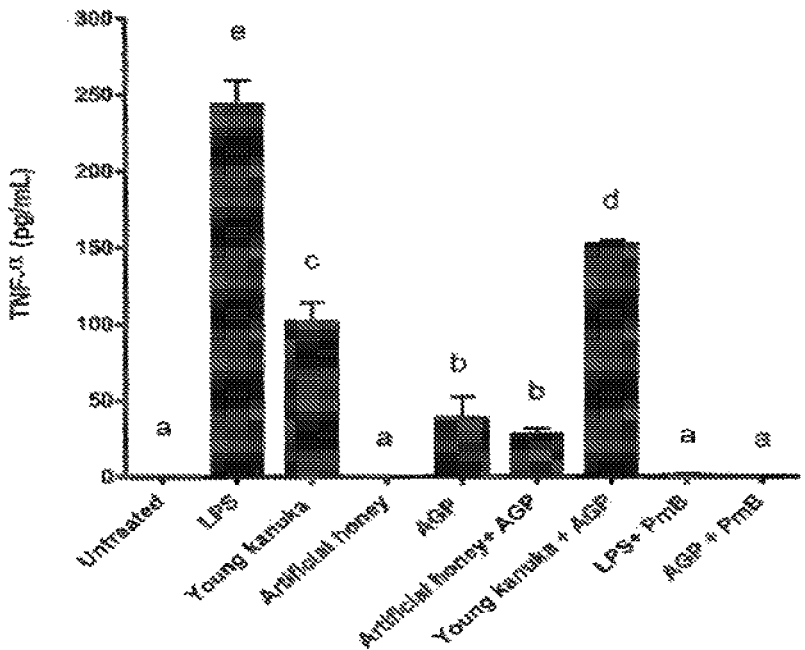
FIG. 10 illustrates a graph showing cytokine production of THP-1 cell line when contacted with varying compositions with and without AGP.

The results found are shown in FIG. 10.

As shown in FIG. 10, a honey analogue without AG produces no inflammatory effects. AGP isolate as expected produces a measurable inflammatory effect. When this isolate was added to the honey analogue, a pro-inflammatory effect resulted as expected.

Trials were completed adding polymyxinB (PmB) to an LPS and AGP isolate composition to confirm the negative effects of polymyxinB on inflammation.

Also tested was a combination of kanuka honey tested as per earlier Examples above but where the kanuka was fortified with the AGP isolate. The resulting impact on cytokine production/inflammation was above that predicted and more than the anticipated additive effect as shown in FIG. 10.

Example 9

In this example, the dose response of AGP isolate was tested and compared to a standard, LPS in terms of pro-inflammatory effects.

Figure 11:
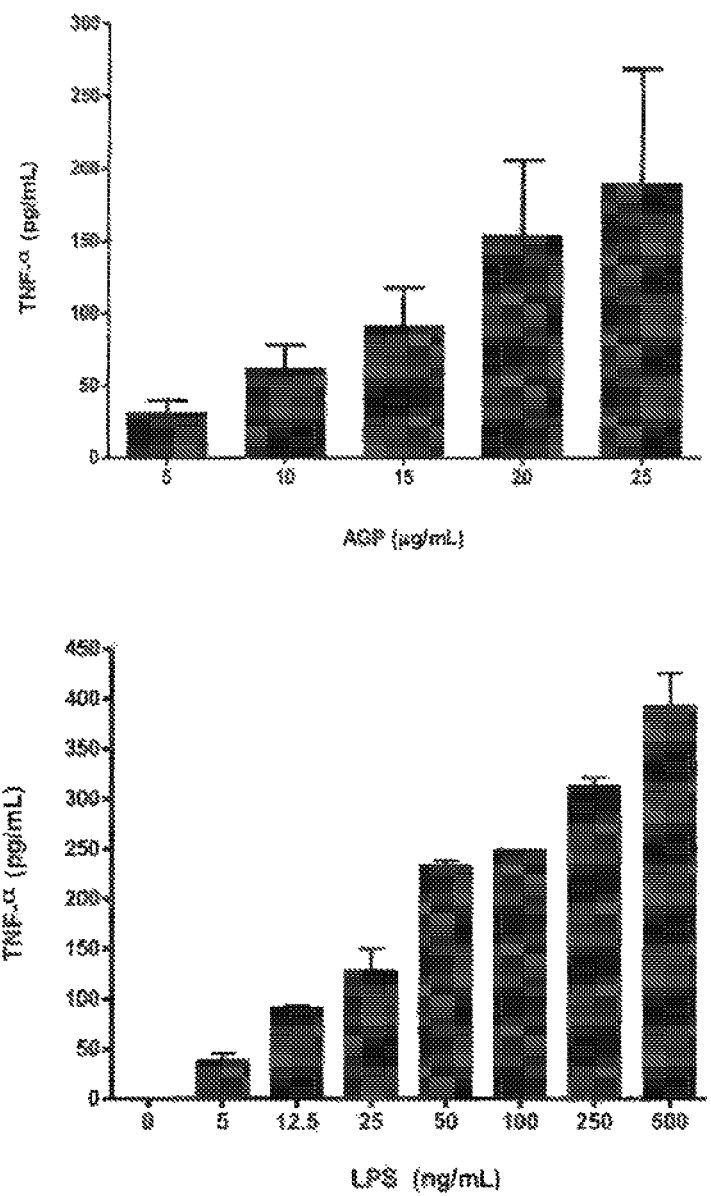
FIG. 11 illustrates a graph illustrating cytokine production as related to dose of AGP isolate.

Varying doses of LPS were tested against THP-1 cell line and the cytokine response measured. An expected linear response was obtained. Subsequent analysis using AGP isolate was then tested and a similar linear response was obtained. Results are shown in FIG. 11 indicating that the immunostimulatory effects appear to transition with a dose of approximately 5 µg/g. This dose or higher doses e.g. 10 µg/g cause a measurable immunostimulatory effect on monocytes while a lower level e.g. less than 1 µg/g result in no or minimal effect on monocytes. The results further reinforce the presence of type II AG compounds and their influence on inflammation.

Example 10

Further characterisation work was completed to determine the make up of the AG compound in the honey.

Fractionation of manuka, kanuka and clover honeys indicated the >10 kDa fraction contained small amounts of type II arabinogalactans (AGs), which are often present as arabinogalactan proteins (AGPs). AGPs were isolated from the >10 kDa fraction of kanuka honey using glucosyl Yariv reagent and their composition and structure analysed. Constituent sugar, glycosyl linkage and NMR spectroscopy analysis of the purified AGP fraction revealed a predominance of neutral sugars, mainly galactose and arabinose, linked in a highly-branched structure typical of type II AGs. The molecular weight of the major component of the purified AGPs was ~110 kDa, as determined by size-exclusion chromatography-multi-angle laser light scattering (SEC-MALLS). The Yariv supernatant fraction contained less total sugar, especially galactose, and more protein than purified AGPs. Linkage analysis indicated this fraction also contained an AG-type polymer in addition to various other polysaccharides and SEC-MALLS indicated the molecular weight of the major component was ~32 kDa.

Example 11

As noted above, isolates may be produced containing type II AG derived from honey.

One method for obtaining such isolates is to separate the type II AG's by using centrifugal ultrafilters (10 to 30 kDa molecular weight cut-off) and the retentate collected being the 10 kDa or greater fraction, termed hereafter as the high molecular weight (HMW) fraction.

Other apparatus capable of 10 to 30 kDa filtration may be used including filtration, ultrafiltration, reverse osmosis, centrifugation and combinations of these process operations.

Example 12

A more detailed protocol used to isolate type II AGP from honey is described.

The protocol comprised three main steps being:
Ultrafiltration with a 10 kDa filter,
Subsequent removal of some proteins by salt precipitation and
Subsequent precipitation of AGP with Yariv reagent.

As may be appreciated, steps after the initial ultrafiltration step above may be omitted if it is not necessary for the isolate to contain highly purified AGP.

Example 13

Examples of varying topical formulations are now provided in Table 1 below.

TABLE 3

Example Topical Formulations

| Formulation Number | Components |
|---|---|
| 1 | A dressing formed from alginate fibre, honey impregnated in the fibre, type II AG isolate mixed into the honey |
| 2 | A dressing formed from cotton gauze fibre, honey impregnated in the fibre, type II AG isolate mixed into the honey |
| 3 | A gel or putty or sheet made from alginate particles mixed with honey and type II AG isolate |
| 4 | A gel or putty or sheet made from carboxymethylcellulose fibre, honey partly to fully impregnated in the fibre, type II AG isolate mixed into the honey |
| 5 | A gel, putty, sheet, cream or ointment made from honey, ethoxylated oil, myristyl myristate or other wax materials such as beeswax and type II AG isolate mixed together |
| 6 | A gel, putty, sheet, cream or ointment made from honey, caprylyl capryl glucoside, myristyl myristate or other wax materials such as beeswax and type II AG isolate mixed together |
| 7 | Honey analogue fortified with type II AG compounds and mixed into a cream base |

Example 14

As noted above, it is also possible to tailor a formulation by testing samples and then selecting samples with either high or low type II AG content and performing subsequent blending steps to either maximise type II AG content in the formulation or instead to minimise type II AG content.

In this example a series of samples are tested and tailored by selection and blending to achieve a desired maximising or minimising.

Ten batches of honey are received at a honey processing premises and samples taken from each honey batch. The samples are analysed to determine the content or otherwise of type II AG in each sample.

Samples with the greatest levels of type II AG are separated and blended together to form a honey with a higher level of inflammatory action. The blended honey may be used to form an isolate by subsequently subjecting the blend to filtration to remove the type II AG compounds.

Samples with lower levels of type II AG or where AG is not present may be selected and blended separately to form a honey with minimal inflammatory action. The blended honey may be used to in medical applications where inflammatory effects are to be avoided such as on a sensitive or open wound or, if the blend has a high MGO content, may be used to instigate and anti-microbial challenge to the wound or other skin ailment but minimise inflammation at the skin site.

Example 15

A detection protocol is now described with which to complete the testing described above.

Antibodies JIM 4, JIM 13, JIM 14, JIM 15, MAC 207, LM 2 and LM 14 were tested. All were useful for an AG-ELISA but JIM 13 yielded significantly better results than the others, having the highest binding capacity.

Sandwich ELISA's were also tested combining the above-mentioned antibodies with a mouse capture antibody for AG. Sandwich ELISA was also successful.

In practice, the protocol found useful is to first bind antibody e.g. JIM 13 to the AG compounds and then detect bound JIM 13 via a secondary antibody such as an anti-rat secondary antibody. From the result, the AG concentration may be derived.

The method described can detect AG concentrations down to 0.5 µg/g and provides linear results between 0.5 and 5 µg/g AG in the sample solution.

Example 16

As noted above it is possible to select and breed plants to influence the content of type II AG in honey produced from the plants.

One method of selection and breeding to increase the content of type II AG compounds in a honey is to test a range of plants ideally from a single species known to already contain significant amounts of AG compounds e.g. kanuka plants, and select for varieties that produce the greatest concentrations of type II AG's in the plant nectar. The plants may then be crossbred with other plant varieties to form 'super' type II AG producing plants. Honey is then produced via bees or artificially from the bred plants and in turn high type II AG honey may be manufactured.

The opposite may also be the case where a low AG content honey is to be produced. Tests may be completed on a range of low AG containing honeys e.g. clover and varieties bred to minimise the AG content and honey produced from these minimised varieties.

Example 17

Breeding and selection methods are described above. An initial screening method may further include selection of plants that provide a challenge for the bee to extract the plant nectar.

Using kanuka honey as an example, kanuka honey is thought to contain more type II AG, because kanuka flowers are narrower than manuka flowers, thereby requiring the bee to extract nectar with greater physical force thereby taking up more AG.

Using this finding, specific breeding for narrow-flowered plants should increase type II AG concentration (as long as the bees are able to access the nectar).

Aspects of the compositions and methods have been described by way of example only and it should be appreciated that modifications and additions may be made thereto without departing from the scope of the claims herein.

What we claim is:

1. A method of minimizing the immune-stimulatory effects of a honey-based topical composition comprising:
   removing type II arabinogalactan from honey in a honey-based topical composition by filtration using a 10 kDa filter;
   wherein the honey-based topical composition is formulated for application to a sensitive topical part on an animal; and
   wherein the honey-based topical composition still provides anti-microbial effects associated with honey after removal of the type II AG from honey in the honey-based topical composition.

2. The method of claim 1, further comprising:
   applying the honey-based topical composition to a sensitive topical part of an animal.

3. The method of claim 2, wherein applying the honey-based topical composition to a sensitive topical part of an animal occurs after applying a different honey-based topical composition to the sensitive topical part of the animal.

4. The method of claim 2, wherein applying the honey-based topical composition to a sensitive topical part of an animal occurs before applying a different honey-based topical composition to the sensitive topical part of the animal.

5. The method of claim 2, wherein the animal is a human.

6. The method of claim 5, wherein the animal is a non-human animal.

7. The method of claim 1, wherein removing type II arabinogalactan from honey in a honey-based topical composition by filtration using a 10 kDa filter comprises removing enough type II arabinogalactan from the honey to reduce the concentration of type II arabinogalactan in the honey to 5 µg/g or less.

8. The method of claim 1, wherein removing type II arabinogalactan from honey in a honey-based topical composition by filtration using a 10 kDa filter comprises removing enough type II arabinogalactan from the honey to reduce the concentration of type II arabinogalactan in the honey to 1 µg/g or less.

9. The method of claim 1, wherein the type II arabinogalactan removed from the honey is type II aragbinogalactan protein.

10. The method of claim 1, wherein the honey from which type II arabinogalactan is removed is clover honey.

11. The method of claim 1, wherein the honey from which type II arabinogalactan is removed is produced from plant nectar selected from the genus *Leptospermum, Kunzea, Weinmannia, Kinghtia, Metrosideros, Fagus, Trifolium, Myrtaceae,* or combinations thereof.

12. The method of claim 1, wherein the honey-based topical composition is formulated as a dressing, a cream, an ointment, a gel, or combinations thereof.

13. The method of claim 1, wherein the honey from which the type II arabinogalactan is removed is manuka honey or kanuka honey.

* * * * *